United States Patent
Colthurst

(10) Patent No.: US 8,948,864 B2
(45) Date of Patent: Feb. 3, 2015

(54) ELECTRICAL TREATMENT APPARATUS

(75) Inventor: James Richard Colthurst, Hungerford (GB)

(73) Assignee: Fenzian Limited (GB)

( * ) Notice: Subject to any disclaimer, the term of this patent is extended or adjusted under 35 U.S.C. 154(b) by 401 days.

(21) Appl. No.: 12/921,120

(22) PCT Filed: Mar. 3, 2009

(86) PCT No.: PCT/GB2009/000590
§ 371 (c)(1),
(2), (4) Date: Feb. 16, 2011

(87) PCT Pub. No.: WO2009/109748
PCT Pub. Date: Sep. 11, 2009

(65) Prior Publication Data
US 2011/0196436 A1    Aug. 11, 2011

(30) Foreign Application Priority Data
Mar. 7, 2008 (GB) .................. 0804332.5

(51) Int. Cl.
*A61N 1/00* (2006.01)
*A61N 1/32* (2006.01)
*A61H 39/00* (2006.01)

(52) U.S. Cl.
CPC .............. *A61N 1/32* (2013.01); *A61H 39/002* (2013.01); *A61H 2201/5043* (2013.01); *A61H 2230/65* (2013.01); *A61N 1/328* (2013.01)
USPC ............................................................ 607/3

(58) Field of Classification Search
USPC ............................................................ 607/3
See application file for complete search history.

(56) References Cited

U.S. PATENT DOCUMENTS

| | | | |
|---|---|---|---|
| 4,966,164 A * | 10/1990 | Colsen et al. | 607/72 |
| 5,173,888 A * | 12/1992 | An | 369/30.27 |
| 5,697,363 A | 12/1997 | Hart | |
| 6,128,537 A * | 10/2000 | Rise | 607/45 |
| 2002/0091049 A1 | 7/2002 | Hisano et al. | |

(Continued)

FOREIGN PATENT DOCUMENTS

| GB | 2 356 052 A | 5/2001 |
|---|---|---|
| GB | 2 414 407 A | 11/2005 |

(Continued)

OTHER PUBLICATIONS

UK Search Report for priority application GB 0804332.5, dated Jul. 2, 2008.
International Search Report for parent application PCT/GB2009/000590, having a mailing date of Jun. 8, 2009.

*Primary Examiner* — Alyssa M Alter
(74) *Attorney, Agent, or Firm* — Andrus Intellectual Property Law, LLP

(57) ABSTRACT

A treatment method and apparatus for performing a diagnostic or therapeutic treatment. The apparatus comprises a treatment head for applying a diagnostic or therapeutic treatment to the body of a patient; means for delivering the treatment through the treatment head; a processor for controlling the treatment; an input arrangement operable by a practitioner to activate the delivery means for initiating the treatment; a sound generator operable at any time before and during the treatment by operation of the or a further input arrangement by the practitioner to generate pleasing sounds; and a speaker for supplying the sounds as output during treatment to distract and hold the attention of the patient.

6 Claims, 3 Drawing Sheets

(56) References Cited

U.S. PATENT DOCUMENTS

| | | |
|---|---|---|
| 2005/0043646 A1 | 2/2005 | Viirre et al. |
| 2005/0194400 A1 | 9/2005 | Berube et al. |
| 2006/0025282 A1 | 2/2006 | Redmann |
| 2007/0276449 A1 | 11/2007 | Gunter et al. |
| 2008/0033229 A1 | 2/2008 | Park |
| 2008/0188779 A1 | 8/2008 | Vallero |

FOREIGN PATENT DOCUMENTS

| | | |
|---|---|---|
| WO | 2005/118061 A1 | 12/2005 |
| WO | 2007/045021 A1 | 4/2007 |
| WO | 2007/129267 A2 | 11/2007 |
| WO | 2007/129267 A3 | 11/2007 |

\* cited by examiner

ELECTRICAL TREATMENT APPARATUS

CROSS-REFERENCE TO RELATED APPLICATIONS

This application is the U.S. national stage application of International Application No. PCT/GB2009/000590, filed Mar. 3, 2009, which International application was published on Sep. 11, 2009, as International Publication No. WO 2009/109748 A1 in the English language, which application is incorporated herein by reference. The International application claims priority of Great Britain Patent Application No. 0804332.5, filed Mar. 7, 2008, which application is incorporated herein by reference.

BACKGROUND

This invention relates to electrical treatment apparatus for the application of a medical diagnostic or therapeutic treatment to individual patients, especially children.

In particular, the invention relates to a handheld device for applying electrical impulses to the body of the patient through the skin for treating a variety of clinical conditions.

The present invention in one aspect is a development of the treatment device disclosed in our earlier published patent application WO 2005/118061, which is incorporated herein by reference.

Various forms of electrical treatment apparatus employing electromagnetic radiation or having electrical control circuitry are well known, and constitute standard equipment in a Doctor's surgery or clinic or in a hospital. For example, it is known to employ handheld scanning devices using electromagnetic radiation for assistance in the diagnosis of certain clinical conditions and in the development of medical treatments. It is also known to employ the handheld device described in our above application for applying a medical therapeutic treatment in a wide variety of clinical conditions by means of electrical stimulus.

When the patient is an adult, the use of such devices is generally straightforward and a doctor or medical assistant simply carries out the required task by placing the patient in the desired treatment position and implementing the steps appropriate to the medical application concerned and according to the function of the device. However, when the patient is a child, problems may arise through the child fidgeting, getting bored and refusing to remain still in the necessary treatment position. This can be a significant problem, since it may compromise the treatment.

SUMMARY

The present invention seeks to provide a new treatment device, which is effective and easy to use and which addresses the problem of applying a diagnostic or medical treatment to a patient, especially a child.

In its preferred form at least, the invention may be applied to a handheld treatment device.

According to the present invention there is provided an electrical device for medical use for diagnostic or treatment purposes, comprising a treatment head for applying a diagnostic or therapeutic treatment to the body of a patient, a control circuit for controlling the treatment, an input arrangement for activating the device, a speaker, and a sound generator operable, for example by the input arrangement, for causing the speaker to emit sounds that are pleasing to a patient, especially a child patient.

Preferably, the sound generator is arranged to store and supply to the speaker sounds selected from amongst: different animal noises, nursery rhymes, popular children's tunes, extracts from children's TV programmes, or fairy tales or other stories.

Advantageously, the sound generator comprises a sound storage memory storing a repertoire of sound themes, a processor for generating a selection command, and a selection circuit responsive to the selection command for selecting for output through the speaker a respective sound from one sound theme in the repertoire of sound themes.

In a preferred form of the invention, the treatment device also comprises a display, and the processor is arranged to respond to an input from the input arrangement by supplying the selection command to the sound generator and an indication to the display of the sound selected for output.

Conveniently, the input arrangement is arranged to co-operate with the processor for providing a scrolling function through the sound themes and the sounds within the themes in the storage memory and for concurrently displaying the scrolled items on the display.

In its preferred form, the treatment device is a handheld battery powered to device.

Preferably, the invention is applied to a handheld treatment device for applying electrical impulses to a living body through the skin, for treating a variety of clinical conditions, comprising: a pair of electrodes for contact with the skin; a waveform generator for repeatedly generating an AC waveform for applying electrical impulses through the electrodes to the skin; a detector for detecting changes in the skin impedance and for generating output signals representing the skin impedance; a monitor responsive to the output signals from the detector for monitoring the responsivity of the skin and for controlling the duration of the application of electrical impulses accordingly.

Preferably, the monitor is arranged to generate a first indication when a predetermined level of responsivity is reached and a second indication when a pre-determined treatment has been administered.

Such a device may have particular application in the treatment of a wide variety of clinical indications in a non-invasive and beneficial manner.

For example, the present invention may be applied to a handheld treatment device for applying electrical impulses of relatively high amplitude and short duration to the body of a patient through the skin for stimulating repair processes within the body, in which the treatment depends on using alternating current electro-stimulation via a biofeedback system based on reaction to skin impedance. The impulses from the device are preferably of short duration (10 μs approx) and of relatively high amplitude (80 v). The influence of the impulses is critically controlled by careful observation using specific measured parameters of the impulses depicted on a display screen of the device. Due to the short duration of each impulse, the energy of the signal is extremely small and harmful effects highly unlikely.

In the preferred embodiment, the skin impedance alterations, which occur as a result of both the local and general state, are depicted numerically on the display during treatment. Moreover, several other operational aspects of the signal exchange between the skin and the treatment device may be depicted numerically on the display (amplitude, rate, gradient, speed and so on). The numerical representations may then be used by the practitioner to guide the treatment processes, via a number of protocols.

In this embodiment, when the processor is also provided with a scrolling function, it is possible for the scrolling function to scroll between the operational representations on the display and a menu for the sound themes.

The present invention has a variety of advantages, not the least of which is that the generation of pleasing sounds during treatment may act as a trigger to relax the patient, and such trigger may be produced at will by the Doctor or other practitioner at moments during the treatment when relaxation may be particularly efficacious.

The device according to the invention also has significant advantages in the treatment of children, in that they can be distracted, during treatment, from potentially painful or upsetting treatment applications, they can be calmed to improve treatment effectiveness, and their attention can be held by the noises, musical phrases or stories issuing from the device to prevent them from becoming bored and fidgety. As a result, they may be more actively involved in their treatment. All of this enhances the ease of use and treatment outcome using the treatment device.

A further aspect of the invention features a method of treating a patient by means of the present treatment device.

According to this aspect of the invention, there is provided a method of treating a patient employing the above electrical device, comprising the steps of: activating the device by operating an input arrangement, applying a diagnostic or therapeutic treatment to the body of a patient through a treatment head of the device, controlling the treatment, and operating a sound generator to cause a speaker to emit sounds that are pleasing to a patient, especially a child patient.

BRIEF DESCRIPTION OF THE DRAWING

The invention is described further, by way of example, with reference to the accompanying drawings, in which.

DETAILED DESCRIPTION OF THE DRAWINGS

Figure 1:
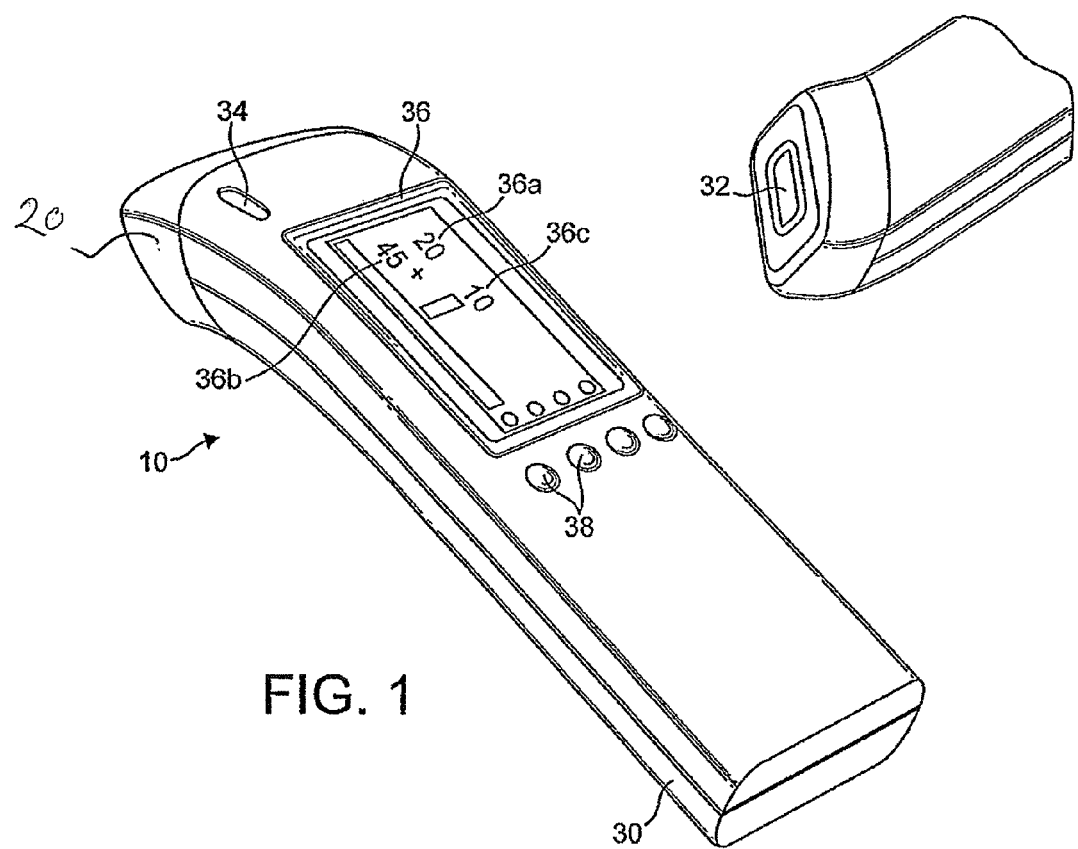
FIG. 1 is a perspective view of a handheld electrical treatment device according to the present invention.
Figure 2:
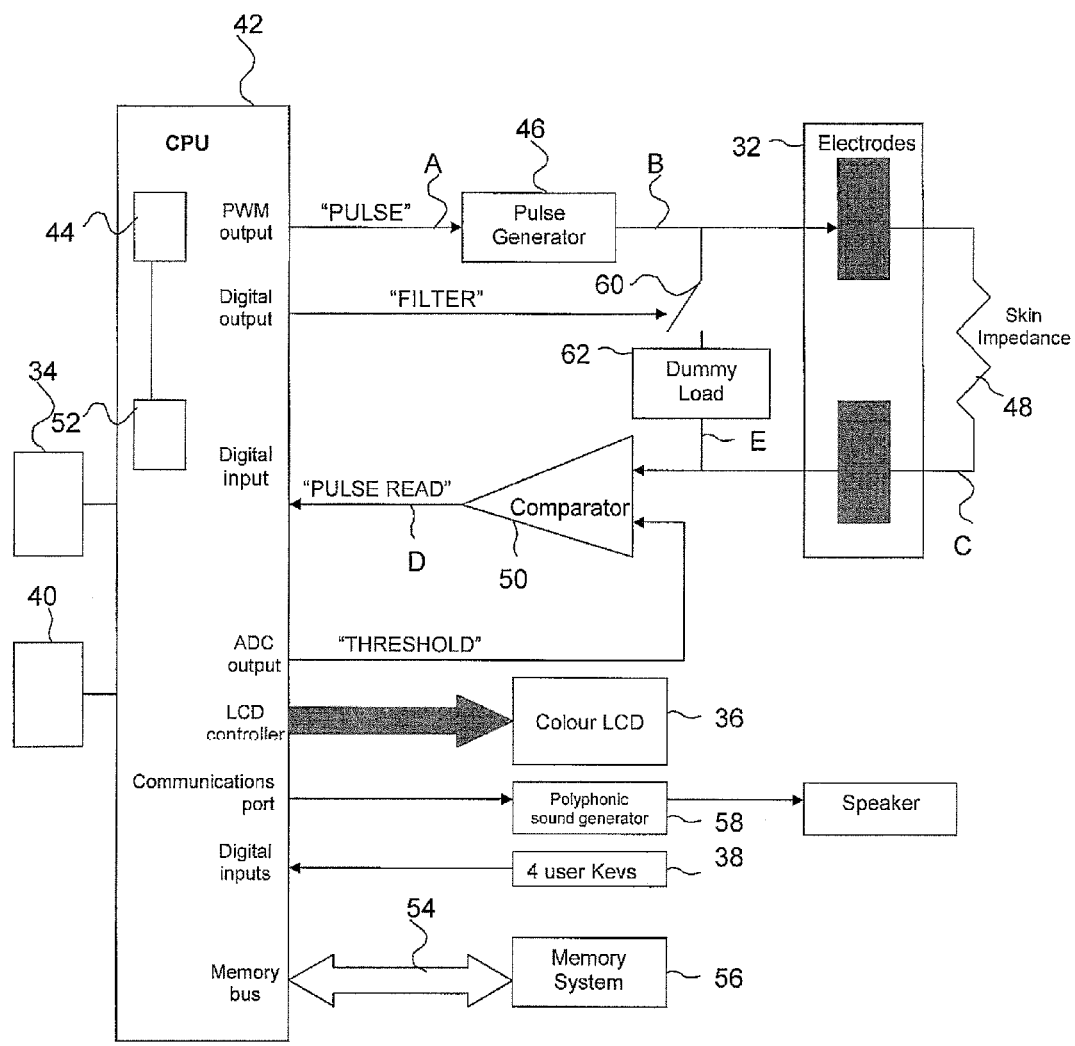
FIG. 2 is a block diagram of the main operating circuitry within the treatment device of FIG. 1.
Figure 3:
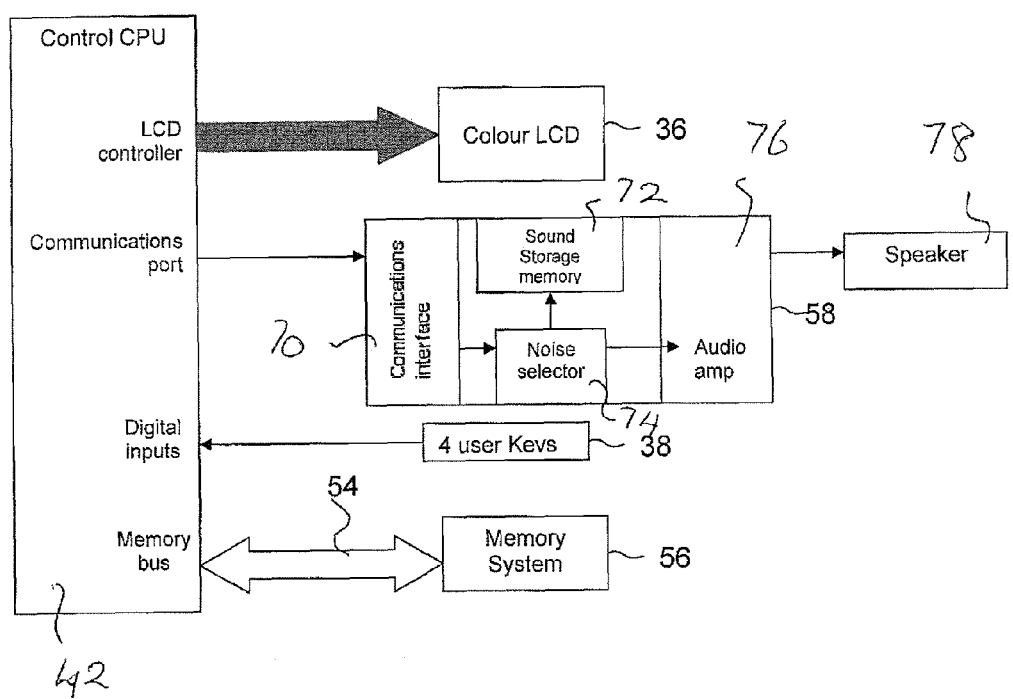
FIG. 3 is a block diagram of circuitry within the device for producing sounds pleasing to a child during treatment.

Referring to FIGS. 1 to 3, the present invention comprises a handheld treatment device 10 for applying electrical impulses to an adult or child patient through the skin. For the purposes of the present description, the treatment of a child by a medical practitioner, who may be a doctor or a nurse for example, will be described.

The treatment device 10 illustrated in FIG. 1 is designed to be placed in contact with the skin and to generate short AC electrical impulses for application to the skin by way of a treatment head 20.

The treatment device 10 comprises a body 30 carrying the treatment head 20, the whole being designed to fit neatly into the hand of the practitioner. The treatment head 20 has a pair of electrodes 32 for applying the treatment, and the body 30 has on its back an on/off switch 34, a display 36 and a series of user control buttons 38. Four such buttons are shown in FIG. 1, but there may be any number depending on the number of different functions that are required to be controlled by the practitioner.

Electrical control circuitry is housed within the body 30 of the treatment device 10 and is shown in FIGS. 2 and 3. Operation of the device 10 is controlled by is the on/off switch 34 and is powered by a battery 40 for applying a treatment in the form of AC electrical impulses through the electrodes 32 to the body of the patient.

As shown in FIG. 2, a central processing unit (CPU) 42 including a clock 44 is arranged to generate an output at point A in the form of a train of rectangular pulses. Such pulses are supplied to a waveform generator 46 for triggering at point B an AC decaying oscillation, which is repeatedly triggered by the pulses from the CPU 42 and which is applied to one of the electrodes 32. A voltage signal is generated across the electrodes 32, effectively at point C, whose magnitude is dependent on whether the electrodes are in open circuit or whether they are in contact with the skin and which is responsive to the skin impedance (represented as a resistor 48). This voltage signal is applied to a comparator 50, where it is compared with a threshold voltage $V_{th}$ output by the CPU 42. The comparator 50 generates a pulse output at point D, in which the rising edge of each pulse corresponds with the voltage from the electrodes 32 increasing above the threshold level and the trailing edge of each pulse corresponds with the voltage from the electrodes 32 falling below the threshold level. A counter 52 within the CPU 42 also connected to the clock 44 counts the clock signal for the duration t of each such pulse and thereby produces a numerical value representing the pulse duration. These numerical values are transmitted by way of a memory bus 54 to a memory or store 56.

Two of the practitioner control keys 38 can be employed for providing inputs to the CPU 42 to cause the CPU 42 to adjust the frequency, duration, and amplitude of the pulses supplied to the waveform generator 46 and to determine whether these pulses are supplied at regular intervals, or repeatedly in clusters. Effectively this is achieved by employing one such user key 38 as a menu control key to activate and scroll through a menu system on the display 36 of the treatment device, and the other such control key to enter the desired parameters. The waveform generator 46 is arranged to respond accordingly for supplying a corresponding AC waveform to the electrodes 32, and in this way the electrical impulses applied to the skin can be adjusted and treatment can be controlled. The CPU 42 processes the information obtained during a treatment session and displays the results on the display 36 as well as storing them in the memory 56. The CPU 42 is also arranged to activate one or more audio indicators 58 for signaling certain events in the treatment session.

In addition, a series connection of a switch 60 and a load 62 is connected across the two electrodes 32 and may be switched into the circuit in response to an output from the CPU 42, either in order to simulate skin contact when the electrodes 32 are not in contact with the skin of a patient or to provide a filter in cases of high skin sensitivity.

In order to obtain a measurement corresponding to skin impedance, ideally the peak voltage values of each of the AC signals obtained at point C would be measured. However, it has been found more practical to measure the duration t of each initial half wave, and for this purpose the comparator 50 generates pulses in response to the crossings of the threshold voltage $V_{th}$ and the counter 52 counts to a numerical value determined in each instance by the generation of each pulse in the signal at the point D. These numerical count values are displayed on the display 36 of the device 10 under the control of the CPU 42.

Referring to FIG. 1, the initial reading for the count value corresponding to the half wavelength t for the first signal occurring at the start of a treatment application is shown at the display location 36a at the top left hand corner of the display 36; the continually varying count value representing the half wavelength t as it changes during a treatment application is shown in the display location 36b in the lower left hand corner of the display 36, and a further count value representing the change of skin impedance with time, i.e. dZ/dt, and derived from counting the rate at which t changes is displayed at the display location 36c on the display 36. At a predetermined moment during treatment, the CPU 42 is arranged to trigger the audio indicator 58 to ring a bell. At the same time, the CPU 42 stops the counter 52 and the count value at the display location 36b is fixed and is stored in the memory 56. At a further predetermined moment during treatment, as represented by the value at the display location 36c showing zero, the CPU 42 is arranged firstly to trigger the audio indicator 58 to sound a buzzer and secondly to terminate generation of the pulse signal A.

According to the invention, in addition to the features already described, a further set of features are provided for causing the treatment device 10 to issue sounds that are pleasing to a child for the purposes of engaging the attention of the child before and especially during treatment. These features are included primarily in the audio indicator 58, and are controlled by the remaining two of the user keys 38 once a sound menu for the production of the child friendly sounds has been selected on the display 36 through use of the menu control key 38 as already described above. These features according to the invention will now be described with reference to FIG. 3.

As shown in FIG. 3, the features of the sound producing system according to the invention are controlled by the two respective user keys 38 in cooperation with the CPU 42 of the treatment device 10. In response to operation of the two user keys 38, the CPU 42 activates the audio indicator 58 to produce child friendly sounds that have the effect of engaging the attention of a child. For this purpose, the audio indicator 58 comprises a communications interface 70 for interfacing with the CPU 42, a sound storage memory 72 in which is stored a repertoire of sound themes, and a noise selector 74 for selecting a respective noise or sound from one of the sound themes stored in the sound storage memory 72. The selected sound is supplied to an audio amplifier 76 and thence to a speaker 78 for output. By way of example only, the sound themes stored in the sound storage memory 72 may include: a selection of different animal noises, a selection of nursery rhymes, spoken or sung, a selection of popular children's tunes, a selection of extracts from popular children's TV programmes, and/or a selection of fairytales or other children's stories.

In a preferred form of the invention, the menu control key 38 is operable to cause the CPU 42 to cycle through the menu system of the treatment device and bring up the sound menu for the production of the child friendly sounds, as already mentioned. After this, one of the two pre-selected user keys 38 acts as a selection key for selecting the sound menu and then the desired sound from within the sound menu and notifying the CPU 42 accordingly. Operation of this pre-selected user key 38 preferably causes the CPU 42 to display a corresponding indication on the display 36.

On selection of the sound menu for the production of a particular sound theme from the sound storage memory 72, the CPU 42 instructs the memory system 56 to store the current operational state of the treatment device 10 and the most current set of readings on the display 36 for the other functions of the device, so that the display 36 can be taken over for the sound selection process. The noise selector 74 then accesses the sound storage memory 72 and supplies to the CPU 42 a list of the available sound themes. The CPU 42 causes the list to be shown on the display 36 and slowly scrolls through the list until the pre-selected user key 38 is operated at a particular item on the display 36, signifying to the practitioner that this item is the sound theme that is selected. In response, the CPU 42 then causes a list of the particular choice of sounds within the selected sound theme to be displayed, and again scrolls slowly through these until the pre-selected user key 38 is operated at a particular item on the display 36, signifying to the practitioner that this item is the sound that is selected. The CPU 42 conveys this to the noise selector 74, which then accesses the associated content in the sound storage memory 72. Operation of the second of the two pre-selected user keys 38 causes the chosen sound to be supplied through the audio amplifier 76 to the speaker 78.

Meanwhile, the CPU 42 times the display of the selected sound on the display 36 and after a predetermined amount of time, for example three seconds, retrieves the previous operational state from the memory system 56 and reverts the display 36 to show this previous state. The CPU 42 always returns the display to its operational view if an amount of time elapses without a selection being made.

The selected sound is then played through the speaker 78 either until the menu control key and the pre-selected user keys 38 are activated again for selection of another sound or until the sound reaches a natural ending on its own.

The basic operation of the handheld treatment device 10 will now be described in the case of a child patient.

Firstly, the physician switches the device on by means of the on/off switch 34 and sets the desired treatment programme as previously described.

Secondly, the practitioner activates the aspect of the sound generation system of the handheld treatment device 10 relating to the production of child friendly sounds by operating the menu control user key 38 to bring up the menu for the child friendly sound generation. The practitioner then activates the first pre-selected user key 38 to select the sound menu, and again operates the menu control key 38 to scroll through the sound themes and sounds stored in the sound storage memory 72, at the same time consulting with the child patient as to which theme and which sound to select. Having selected one theme, the practitioner starts the sound playing by activating the second pre-selected key 38 and allows the display 36 to revert to its previous treatment mode, and commences treatment.

Next, the physician selects an area of the body for treatment and applies the electrical impulses to different body zones within this area. A number of initial readings will thus be generated and stored in the memory 56, and from the readings on the display location 36a the physician will select a number of zones with relatively high initial readings, representing relatively high skin impedances, and will apply a treatment dose until the audio indicator 58 rings the bell. A new series of readings displayed at the display location 36b is thus generated and stored in the memory 56. The physician now selects the highest one of these second series of readings, and applies a further set of electrical impulses until the audio indicator 58 sounds the buzzer. At this moment, a final reading is obtained as shown at the display location 36b corresponding to a zero at the display location 36c, and this final reading is also stored in the memory 56.

At any moment during treatment, the practitioner may interrupt the treatment to select a further child friendly sound, as already described, and may then allow the display to revert to its previous operational condition to continue the treatment.

In the preferred embodiment of the invention, the physician will in practice follow a precise treatment plan under the guidance of the CPU 42.

In the described embodiment, the handheld device 10 is arranged to apply electrical impulses to the skin of the patient for treating the patient for a variety of clinical conditions. However, it will be appreciated that various modifications are possible within the scope of the invention.

For example, the circuitry of FIG. 3 can be employed in any other handheld medical treatment device for supplying sounds for the purposes of distracting, or drawing or engaging the attention of, a child before or during a medical diagnostic or therapeutic treatment.

The invention may also be applied to treatment apparatus, in which a handheld treatment head for applying a treatment is connected to but separate from a computer including a processor for controlling treatment. In this instance, means for delivering the treatment to the treatment head, an input arrangement for initiating treatment and the generation of sounds, and the sound generator may be distributed between the treatment head and the computer. The treatment head may be connected to the computer by a cable, or wirelessly eg by Wi-Fi, or by any other conventional connection arrangement.

The circuitry of FIG. 3 may also be employed generally in other medical treatment apparatus that is not handheld.

FIG. 3 shows an arrangement in which the sound storage memory 72 and noise selector 74 are separate from the processor 42. Of course, these circuits could alternatively be situated within the processor 42 itself.

Other possible variants include the replacement of the display 36 with a different visual indicator, and the replacement of the user keys or control buttons 38 with a different input arrangement.

Likewise, the scrolling function for selection of a particular sound and sound theme, which is currently provided through depression of one of the pre-selected user keys 38 activating the CPU 42 to achieve a scrolling function, can be replaced by an arrangement according to which the CPU 42 causes the entire list to be displayed on the screen 36 together with a control slide or wheel for moving a cursor on the screen to select one theme from the list.

The treatment device according to the present invention offers significant advantages in the treatment of children, in that it offers an entertainment function for the child to engage the interest of or distract the child during treatment. This may have a calming effect and aid in the treatment, or at the very least it may stop the child from fidgeting and disrupting the treatment.

What is claimed is:

1. A treatment apparatus for performing a diagnostic or therapeutic treatment, comprising:
   a handheld treatment device comprising:
      a body and treatment head together configured to fit into a hand of a practitioner, the treatment head for applying electrical impulses through the skin of a patient for effecting a diagnostic or therapeutic treatment, and the body carrying the treatment head;
      delivery means for delivering the treatment through the treatment head; and
      an input arrangement on the body of the treatment device operable by the practitioner for initiating and adjusting treatment;
   a control circuit including a processor for controlling the treatment;
   a sound generator that operates independently of the delivery means to generate a sound, the sound generator including sound storage memory storing a repertoire of sound themes, means in the processor for generating a selection command, and a selection circuit responsive to the selection command for selecting a respective sound from one of the sound themes from the sound storage memory for output;
   a display controlled by the processor to display treatment parameters, and to cause a menu of sounds in the repertoire of sound themes to be produced by the display and to revert from the display of the menu to a previous display state after a predetermined time period;
   the input arrangement being operable by the practitioner to cause the processor to activate the delivery means for initiating the treatment and being further independently operable by the practitioner at any time before and during the treatment to select the sound from the repertoire of sound themes to be generated by the sound generator; and
   a speaker for supplying the generated sound as output to the patient being treated;
   wherein the repertoire of sound themes includes at least one sound theme from the group comprising: animal noises, nursery rhymes, popular children's tunes, extracts from TV programs, and stories.

2. A treatment apparatus according to claim 1, in which the arrangement activates the processor to generate the selection command.

3. A treatment apparatus according to claim 1, in which the processor causes the menu to scroll across the display responsive to a scroll command from the input arrangement.

4. A treatment apparatus according to claim 1, in which the treatment head comprises a pair of electrodes for contact with the skin; and further comprising;
   a waveform generator for repeatedly generating an AC waveform for applying electrical impulses through the electrodes to the skin; and
   a detector for receiving a feedback signal from the skin and for generating output signals representing the skin impedance in which the processor comprises a monitor responsive to the output signals from the detector for monitoring the responsivity of the skin and for controlling the duration of the application of the electrical impulses.

5. A method of engaging the attention of a patient while performing a diagnostic or therapeutic treatment, comprising:
   employing a handheld treatment device for applying a diagnostic or therapeutic treatment, the handheld treatment device comprising a body and a treatment head together configured to fit into the hand of a practitioner, the treatment head applying electrical impulses through the skin to the body of a patient;
   controlling delivery of the treatment through the treatment head by means of a processor;
   activating an input arrangement on the handheld treatment device to initiate and adjust the treatment;
   presenting on a display respectively treatment parameters and a menu of sound themes;
   receiving a selection from the input arrangement of a sound theme from the menu at any time before and during the treatment;
   reverting the presentation of the menu on the display state after a predetermined time period;
   independently of the activation of the input arrangement to initiate treatment activating a sound generator, which includes a sound storage memory storing a repertoire of sound themes and a selection circuit responsive to the received selection of the sound theme, for selecting a respective sound from one of the sound themes from the sound storage memory for output, at any time before and during the treatment, in order to produce the selected sound theme; and
   supplying sounds of the selected sound theme through a speaker as output to the patient being treated;
   wherein the repertoire of sound themes includes at least one sound theme from the group comprising: animal noises, nursery rhymes, popular children's tunes, extracts from TV programs, and stories.

6. A treatment device for performing a diagnostic or therapeutic treatment, comprising:
  an input arrangement operable by a practitioner to receive a first user input for initiating treatment and independently operable by the practitioner at any time before and during treatment to receive a second user input to select a sound from a repertoire of sound themes;
  a treatment head configured to apply a diagnostic or therapeutic treatment to the body of a patient in response to the first user input applied to the input arrangement;
  a display having at least a first state in which information concerning the treatment is displayed and a second state in which a menu system of sounds in the repertoire is displayed on the display;
  a processor arranged to control the treatment applied by the treatment head, the processor being arranged to control the display, in response to the second user input selectively received by the input arrangement at any time, to the second state displaying the menu system on the display, and to receive a selection of sound theme from a menu of sounds in the repertoire of sound themes, and to control the display to alter from the second state displaying the menu of sounds to the first state displaying information concerning the treatment after a predetermined time period;
  a sound generator that operates independently of the treatment head and including sound storage memory storing the repertoire of sound themes and a selection circuit responsive to a selection command from the processor for selecting a respective sound from one of the sound themes from the sound storage memory to generate the selected sound theme; and
  a speaker for supplying sounds of the selected sound theme as output;
  wherein the repertoire of sound themes includes at least one sound theme from the group comprising: animal noises, nursery rhymes, popular children's tunes, extracts from TV programs, and stories.

* * * * *